United States Patent [19]

Berg et al.

[11] Patent Number: 5,128,121
[45] Date of Patent: Jul. 7, 1992

[54] MIXTURE OF A POSITIVE AND NEGATIVE CONTRAST AGENT FOR MAGNETIC RESONANCE IMAGING

[75] Inventors: Arne Berg, Blommenholm; Jo Klaveness, Oslo, both of Norway

[73] Assignee: Nycomed AS, Oslo, Norway

[21] Appl. No.: 585,140

[22] PCT Filed: Apr. 6, 1989

[86] PCT No.: PCT/EP89/00376
§ 371 Date: Oct. 9, 1990
§ 102(e) Date: Oct. 9, 1990

[87] PCT Pub. No.: WO89/09625
PCT Pub. Date: Oct. 19, 1989

[30] Foreign Application Priority Data

Apr. 8, 1988 [GB] United Kingdom ............... 8808305

[51] Int. Cl.$^5$ .............. G01N 31/00; G01N 24/00; A61K 31/27; A61K 31/28
[52] U.S. Cl. ..................... 424/9; 424/646; 424/648; 514/492; 514/505; 514/836; 436/173; 128/653.4; 128/653.3
[58] Field of Search .............. 424/9, 646, 647, 648; 514/505, 492, 836; 436/173; 128/653 R, 653 AF, 653 CA, 654

[56] References Cited

U.S. PATENT DOCUMENTS

| | | | |
|---|---|---|---|
| 3,731,377 | 5/1973 | Muckelroy | 29/834 |
| 4,247,398 | 1/1981 | Mohri | 210/222 |
| 4,590,922 | 5/1986 | Gordon | 600/10 |
| 4,735,796 | 4/1988 | Gordon | 424/9 |
| 4,813,399 | 3/1989 | Gordon | 600/12 |
| 4,827,945 | 5/1989 | Groman et al. | 128/653 R |
| 4,889,120 | 12/1989 | Gordon | 606/216 |

OTHER PUBLICATIONS

Carvlin et al., Society for Magnetic Resonance Imaging, 5th Annual Meeting, San Antonio, Texas, 1987.
Weissleder et al., *AJR*, 150, 561–566 (1988).

*Primary Examiner*—Glennon H. Hollrah
*Assistant Examiner*—Gary E. Hollinden
*Attorney, Agent, or Firm*—Bacon & Thomas

[57] ABSTRACT

There is provided a method of generating enhanced images of the human or non-human animal body, for example for use in medical diagnosis, which involves administering to the body a positive MRI contrast agent which is body tissue- or body duct-specific following the particular mode of administration and a negative MRI contrast agent which preferably also is body tissue- or body duct-specific. Thereafter a magnetic resonance image is generated of a part of the body containing the negative and positive contrast agents or their paramagnetic, ferromagnetic or superparamagnetic biodegradation products. Contrast media suitable for use in this new image generating method are also provided.

17 Claims, 3 Drawing Sheets

MIXTURE OF A POSITIVE AND NEGATIVE CONTRAST AGENT FOR MAGNETIC RESONANCE IMAGING

This invention relates to improvements in and relating to magnetic resonance imaging (MRI) and more particularly to a novel method of enhancing contrast in MRI and to contrast media therefor.

In MRI, the contrast in the images generated may be enhanced by introducing into the zone being imaged an agent, generally referred to as a contrast agent, which affects the spin reequilibration characteristics of the nuclei (the "imaging nuclei" which generally are protons and more especially water protons) which are responsible for the resonance signals from which the images are generated. The enchanced contrast obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents.

The majority of materials now being proposed as MRI contrast media achieve a contrast effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration coefficient known as $T_2$ or as the spin-spin relaxation time, a reduction arising from the effect on the imaging nuclei of the fields generated by the ferromagnetic or superparamagentic particles.

Paramagnetic contrast agents on the other hand may be either positive or negative MRI contrast agents. The effect of paramagnetic substances on magnetic resonance signal intensities is dependent on many factors, the most important of which are the concentration of the paramagnetic substance at the imaged site, the nature of the paramagnetic substance itself and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where their $T_2$ lowering effect is dominant. In either event, the relaxation time reduction results from the effect on the imaging nuclei of the magnetic fields generated by the paramagnetic centres.

The use of paramagnetic, ferromagnetic and superparamagnetic materials as MRI contrast agents has been widely advocated and broad ranges of suitable materials have been suggested in the literature.

Thus, for example Lauterbur and others have suggested the use of manganese salts and other paramagnetic inorganic salts and complexes (see Lauterbur et al. in "Frontiers of Biological Energetics", volume 1, pages 752-759, Academic Press (1978), Lauterbur in Phil. Trans. R. Soc. Lond. B289: 483-487 (1980) and Doyle et al. in J. Comput. Assist. Tomogr. 5(2): 295-296 (1981)), Runge et al. have suggested the use of particulate gadolinium oxalate (see for example U.S. Pat. No. 4,615,879 and Radiology 147(3): 789-791(1983)), Schering AG have suggested the use of paramagnetic metal chelates, for example of aminopolycarboxylic acids such as nitrilotriacetic acid (NTA), N,N,N',N'-ethylenediaminetetraacetic acid (EDTA), N-hydroxyethyl-N,N',N'-ethylenediaminetriacetic acid (HEDTA), N,N,N',-N'',N''-diethylenetriaminepentaacetic acid (DTPA), and 1,4,7,10-tetraazacyclododecanetetraacetic acid (DOTA) (see for example EP-A-71564, EP-A-130934, DE-A-3401052 and U.S. Pat. No. 4,639,365), and Nycomed AS have suggested the use of paramagnetic metal chelates of iminodiacetic acids (see EP-A-165728). Besides paramagnetic metals, paramagnetic stable free radicals have also been suggested for use as positive MRI contrast agents (see for example EP-A-133674).

Other paramagnetic MRI contrast agents are suggested or reviewed in, for example, EP-A-136812, EP-A-185899, EP-A-186947, EP-A-292689, EP-A-230893, EP-A-232751, EP-A-255471, WO85/05554, WO86/01112, WO87/01594, WO87/02893, U.S. Pat. No. 4,639,365, U.S. Pat. No. 4,687,659, U.S. Pat. No. 4,687,658, AJR 141: 1209–1215 (1983), Sem. Nucl. Med. 13: 364 (1983), Radiology 147: 781 (1983), J. Nucl. Med. 25: 506 (1984), WO89/00557 and International Patent Application No. PCT/EP89/00078.

Ferromagnetic (a term used herein to cover both ferrimagnetic and ferromagnetic materials) and superparamagnetic MRI contrast agents, for example subdomain sized magnetic iron oxide particles either free or enclosed within or bound to a particle of a non-magnetic matrix material such as a polysaccharide, are disclosed by Schröder and Salford in WO85/02772, by Nycomed AS in WO85/04330, by Widder in U.S. Pat. No. 4675173, by Schering AG in DE-A-3443252 and by Advanced Magnetics Inc in WO88/00060.

Intravenous administration, at separate times, of the positive contrast agent Gd DTPA-dimeglumine (which following such administration rapidly distributes extracellularly) and of superparamagnetic ferrite particles was proposed by Weissleder et al. in AJR 150: 561–566 (1988) for imaging of liver cancers and by Carvlin et al. Society for Magnetic Resonance Imaging, 5th Annual Meeting, San Antonio, 1987, for studying renal blood-flow. Carvlin and Weissleder's work on this topic is reported further in Proc. SPIE-Int.Soc.Opt.Eng. (1988) 914 Medical Imaging II, Pages 10–19 and AJR 150 115-120 (1988) respectively.

The present invention arises from the recognition that tissue or organ visualization in MRI may surprisingly be particularly enhanced by administration of tissue- or body duct-specific positive and negative contrast agents, despite their diametrically opposed contrast effects.

Thus, in one aspect, the present invention provides the use of body tissue- or body duct-specific positive and negative MRI contrast agents e.g. a physiologically acceptable paramagnetic substance and a physiologically acceptable ferromagnetic or superparamagnetic substance, for the manufacture of a contrast medium for use in a method of diagnosis practised on the human or non-human animal body, a which method comprises administering to said body a body tissue- or body duct-specific negative MRI contrast agent and a body tissue- or body duct-specific positive MRI contrast agent and generating a magnetic resonance image of a part of said body containing said negative and positive contrast agents or paramagnetic, ferromagnetic or superparamagnetic biodegradation products thereof.

In a further aspect, the present invention provides the use of a body tissue- or body duct specific positive MRI contrast agent, e.g. a physiologically acceptable paramagnetic substance, for the manufacture of a contrast medium for use in a method of diagnosis practised on the human or non-human animal body, which method comprises administering to said body a body tissue- or body duct-specific negative MRI contrast agent and a said positive MRI contrast agent and generating a magnetic resonance image of a part of said body containing said negative and positive contrast agents or paramagnetic, ferromagnetic or superparamagnetic biodegradation products thereof.

In a yet further aspect, the present invention provides the use of a body tissue- or body duct-specific negative MRI contrast agent, e.g. a physiologically acceptable ferromagnetic or superparamagnetic substance, for the manufacture of a contrast medium for use in a method of diagnosis practised on the human or non-human animal body, which method comprises administering to said body a said negative MRI contrast agent and a body tissue- or body duct-specific positive MRI contrast agent and generating a magnetic resonance image of a part of said body containing said negative and positive contrast agents or paramagnetic, ferromagnetic or superparamagnetic biodegradation products thereof.

In a still further aspect, the present invention provides a method of diagnosis practised on the human or non-human animal body, which method comprises administering to said body an effective amount of a body tissue- or body duct-specific negative MRI contrast agent and an effective amount of a body tissue- or body duct-specific positive MRI contrast agent, e.g. a physiologically acceptable paramagnetic substance and a physiologically acceptable ferromagnetic or superparamagnetic substance, and generating a magnetic resonance image of a part of said body containing said paramagnetic substance and said ferromagnetic or superparamagnetic substance or paramagnetic, ferromagnetic or superparamagnetic biodegradation products thereof.

In a yet still further aspect the invention provides a method of generating images of the human or non-human animal body, which method comprises administering to said body a body tissue- or body duct-specific negative MRI contrast agent and a body tissue- or body duct-specific positive MRI contrast agent, e.g. a physiologically acceptable paramagnetic substance and a physiologically acceptable ferromagnetic or superparamagnetic substance, and generating a magnetic resonance image of a part of said body containing said negative and positive agents or paramagnetic, ferromagnetic or superparamagnetic biodegradation products thereof.

By tissue or duct specific it is meant that the agent and administration route are such that following administration the agent does not distribute widely but instead is substantially maintained within a body duct or cavity throughout the period necessary for image generation or is caused to concentrate at a particular body tissue or organ due to the interaction of the body and the agent. Thus particularly preferably the tissue or duct specific agent may be a blood pool agent administered into and then retained within the cardiovascular system (unlike the extracellularly distributing GdDTPA which after iv administration rapidly distributes into a body volume about five times larger than that of the circulatory system). In another preferred embodiment, the tissue or duct specific agent is a tissue targetting agent, such as the hepatobiliary positive contrast agents of EP-A-165728 or the reticuloendothelial system targetting negative contrast agents of WO85/04330. However, for the purposes of the methods according to the invention extracellularly-distributing paramagnetic metal-containing positive contrast agents, such as Gd DTPA, Gd DOTA and Gd DTPA-BMA (the gadolinium chelate of the bismethylamide of DTPA), may be used according to the present invention for administration into body cavities or tracts having externally voiding ducts, e.g. for oral administration into the gastrointestinal tract, since they are not absorbed into the body from such cavities or tracts and using such administration routes can be considered to be "duct specific".

In accordance with the invention, the positive and negative contrast agents are duct or tissue specific. Particularly preferably the specificity of the agents should be such that at the sites of particular interest for imaging the two should distribute within different body volumes Where the agents are administered via the same administration route, e.g. into the cardiovascular system, this will mean that operation of the body organ or tissue to separate the agents will result in enhanced contrast of the agents. Alternatively, however, the agents can be administered via different routes and caused to approach each other or to merge in the body region being imaged.

In one particularly preferred embodiment of the method and use of the invention, the positive and negative contrast agents are administered together as a single composition and in a still further aspect the invention thus provides a magnetic resonance imaging contrast medium composition comprising at least one physiologically acceptable body tissue- or body duct-specific negative MRI contrast agent together with at least one physiologically acceptable body tissue-or body duct-specific positive MRI contrast agent, e.g. at least one physiologically acceptable paramagnetic substance together with at least one physiologically acceptable ferromagnetic or superparamagnetic substance, preferably also together with at least one physiologically acceptable carrier or excipient.

The paramagnetic substance used according to the present invention may be any one of the physiologically tolerable paramagnetic substances already proposed for use as MRI contrast agents. Preferably, it will be a chelate complex of a paramagnetic atom or ion, for example a lanthanide or transition metal atom or ion, or a stable free radical. Conveniently, the paramagnetic species will have an atomic number of 21 to 29, 42, 44 or 57 to 71. As positive MRI contrast agents, metal chelates in which the metal species is Eu, Gd, Dy, Ho, Cr, Mn or Fe are especially preferred and $Gd^{3+}$, $Cr^{3+}$, $Fe^{3+}$ and $Mn^{2+}$ are particularly preferred. As negative MRI contrast agents, metal chelates in which the paramagnetic metal species is $Tb^{3+}$ or $Sm^{3+}$ or more especially $Dy^{3+}$ are particularly preferred, e.g. Dy DTPA-BMA, or DyDTPA-beta-alanine-dextran (molecular weight 70000) where a blood pooling positive contrast agent is desired.

As mentioned above, the paramagnetic species is preferably present in the form of a chelate and chelates in which the chelating atoms are nitrogen, oxygen or sulphur are particularly suitable and those in which the chelating moiety is a carboxylic acid or aminocarboxylic acid moiety are especially preferred.

In general, the chelating moiety in the paramagnetic substance may conveniently be the residue of a conventional metal chelating agent. Suitable such agents are well known from the literature relating to MRI contrast agents discussed above (see for example EP-A-71564, EP-A-130934, EP-A-186947, U.S. Pat. No. 4639365 and DE-A-3401052) as well as from the literature relating to chelating agents for heavy metal detoxification. The chelating moiety chosen is preferably one that is stable in vivo and is capable of forming a chelate complex with the selected paramagnetic metal species. Preferably however, the chelating moiety will be one as described in EP-A-186947 or the residue of an aminopoly(carboxylic acid or carboxylic acid derivative) or a salt thereof, for example one of those discussed by Schering AG in EP-A-71564, EP-A-130934 and DE-A-3401052 and by Nycomed AS in WO 89/00597.

Particularly preferred as chelating moieties for the hydrophilic paramagnetic substances used in the present invention are the residues of the following: EDTA; DTPA-BMA; DOTA; desferrioxamine; and the physiologically acceptable salts thereof.

Where the chelating moiety in a paramagnetic substances used according to the present invention has a labile counterion, that counterion should be a physiologically tolerable ion, for example the ion of an alkali metal, a non-toxic amine (for example tris(hydroxymethyl)aminomethane, ethanolamine, diethanolamine and N-methylglucamine), a halogen, or a non-toxic organic or inorganic acid.

Furthermore, a paramagnetic substance used according to the invention may particularly conveniently comprise a paramagnetic species bound by a chelating entity, itself bound to a larger mass, for example a soluble or insoluble polysaccharide macromolecule or a biomolecule which is capable of targetting the paramagnetic species onto a specific organ or tissue within the body. In such instances, it may be advantageous to have the chelating entity bound to the macromolecule or biomolecule through the agency of an intermediate or linker molecule and it may be particularly advantageous to utilize a linker molecule which forms or contains a biodegradable bond so that the paramagnetic centre may be released for excretion from the body or for uptake by particular organs or tissues.

Binding a paramagnetic metal chelate to a larger mass also has the effect of increasing its contrast effect enhancing ability by reducing the tumbling motion of the paramagnetic centres.

Thus for a paramagnetic negative MRI contrast agent, if uniform distribution after i.v. administration is desired, one may conveniently use as the chelating moiety a hydrophilic extracellular substance, such as DTPA or DOTA or a chelating agent as claimed in WO89/00557. However, to achieve tissue- or duct-specificity, for either positive or negative MRI contrast agents it may instead be desired to use a paramagnetic substance with blood-pooling properties and in this regard it may be suitable to use a chelated paramagnetic species bound to biologically passive or biologically tolerable macromolecules, for example proteins such as albumin or polysaccharides such as dextrans and cellulose derivatives, having molecular weights above the kidney threshold, preferably of about 40000 or more. Alternatively, where targetting of a paramagnetic substance onto a specific tissue is desired, the paramagnetic species may be bound to a tissue- or organ-specific biomolecule, for example an antibody, or to chelating agents which cause the paramagnetic substance to locate at particular tissues, for example the meglumine salt of the chromium (III) chelate of N-(2,6-diethylphenylcarbamoylmethyl)iminodiacetic acid (CrHIDA), the iron (III) chelate of ethylene -bis(2-hydroxyphenylglycine)(known as FeEHPG—see Lauffer et al. Journal of Computer Assisted Tomography 9: 431 (1985)), manganese chelates such as the hepatobiliary $Mn^{2+}$ chelate of N,N'-bis (pyridoxal-5-phosphate)-ethylenediamine-N,N'-diacetic acid (Mn DPDP—see Worah et al. Society of Magnetic Resonance in Medicine, Sixth Annual Meeting, New York, 1987, Works in Progress, page 16) and the tumor specific $Mn^{3+}$ chelate of mesotetra (4-sulphonato-phenyl) porphine (Mn TPPS$_4$)(see Button et al. Society of Magnetic Resonance in Medicine, Sixth Annual Meeting, 1987, Vol. 2 Book of Abstracts, page 660), lipophilic gadolinium chelates such as B-19036 (see Vittadini et al. Society of Magnetic Resonance in Medicine, Sixth Annual Meeting, 1987, Vol. 1 Book of Abstracts, page 322 and also EP-A 230893) or other substances which are taken up by the hepatobiliary system or other tumour specific agents such as paramagnetic porphyrin derivatives.

A wide range of suitable paramagnetic substances is described in the patents, patent applications and journal articles referred to above, the disclosures of which are incorporated herein by reference.

Ferromagnetic or superparamagnetic substances used according to the invention may conveniently comprise particles of a magnetic metal or alloy, for example of pure iron, or of a magnetic compound, for example magnetic iron oxides such as magnetite, gamma-ferrite and cobalt, nickel or manganese ferrites. These particles may be free or may be coated by or carried in or on particles of a non-magnetic matrix material. If free, the particles should preferably be of sufficiently small size as to be superparamagnetic, for example 5 to 50 nm. The particles of the superparamagnetic or ferromagnetic material may be coated or carried in or on particles of a non-magnetic matrix material, for example of a polysaccharide such as dextran, starch or a protein such as albumin and when targetting of the ferromagnetic or superparamagnetic substance onto a specific tissue is desired it may be desirable to use a ferromagnetic or superparamagnetic material which is bound to a tissue- or organ-specific biomolecule (see for example Renshaw et al. Magnetic Resonance Imaging 4: 351-357 (1986)). The overall particle size will preferably be less than about 100 micrometers if the particles are to be administered orally and less than 5.0 micrometers if the particles are to be administered intravenously. For intravenous administration, the mean overall particle size will preferably be in the region of 0.01 to 1.5 micrometers, while for administration directly into the digestive tract (for example orally) or into the bladder, the uterus, the biliary duct or the parotid duct, the mean overall particle size will preferably be 0.01 to 50 micrometers, especially 0.1 to 2.0 micrometers.

Where the superparamagnetic or ferromagnetic material is provided with a non-magnetic coating or matrix, the coating or matrix material is particularly preferably a protein or a starch or polysaccharide material as suggested Schröder in WO83/01738 or a biotolerable polymer such as is suggested by Ugelstad et al. in WO83/03920. Biodegradable coating or matrix materials such as suggested by Schröder are particularly preferred for particles which are to be administered parenterally while the polymer matrices and coating materials of Ugelstad are particularly preferred for oral administration.

Where the ferromagnetic or superparamagnetic material is provided with a coating or matrix, the iron content of the overall particles will preferably be from 0.1 to 80%, more preferably at least 1%, especially 5 to 70%, by weight.

As with the paramagnetic substances discussed above, a wide range of ferromagnetic and superparamagnetic substances is suggested in the patents, patent applications and journal articles mentioned above, the disclosures of which are also incorporated herein by reference.

The positive and negative contrast agents may be administered either together or separately and either parenterally or enterally, e.g. directly into a body cavity having an external evacuation duct, for example orally or rectally or, generally by catheter, directly into the bladder or uterus. Generally, the positive and negative MRI contrast agents will be administered into the same body duct, organ or cavity, for example both may be administered intravenously; nevertheless in certain circumstances it may be desirable to select different administration routes for the positive and negative contrast agents and to image body sites where the separately administered agents approach or merge. Consequently, the contrast media administered to the patient are conveniently either unitary compositions containing both positive and negative contrast agents or are separate compositions one containing at least one negative contrast agent and another containing at least one positive contrast agent and in a further aspect the present invention also provides a MRI contrast medium kit comprising a first container containing a positive MRI contrast medium (e.g. a paramagnetic substance, together with at least one physiologically acceptable carrier or excipient, for example water for injections) in an administration form adapted for body tissue- or body duct-specific contrast enhancement and a second container separately containing a negative MRI contrast medium (e.g. a superparamagnetic or ferromagnetic substance together with at least one physiologically acceptable carrier or excipient) in an administration form adapted for body duct- or body tissue-specific contrast enhancement. Particularly conveniently the positive and negative media in the kit of the invention are adapted for administration into different body tissues, ducts or cavities.

The kit of the invention may be used for the separate administration of the positive and negative contrast agents or the positive and negative contrast agents from a kit may be mixed and administered together.

Thus, for example, the kit of the invention might conveniently contain two intravenous contrast agents, for example a dispersion of intravenously administrable ferromagnetic or superparamagnetic particles and an intravenously administrable solution of a soluble dextran-bound gadolinium chelate, or the kit might contain an orally administrable contrast agent and an intravenous contrast agent, for example a dispersion or suspension of magnetic particles for administration into the gastrointestinal tract and an intravenous solution containing a paramagnetic substance which will target onto the pancreas. Alternatively, to obtain systemic contrast enhancement, an orally administrable non-absorbable negative contrast agent and an orally administrable absorble paramagnetic substance might be used, either formulated together as a single composition or formulated separately, for example for packaging together as a kit according to the invention.

The method of the present invention appears to be particularly promising insofar as the imaging of the hepatobiliary system is concerned.

Thus it has been shown in animal experiments that intravenous administration of superparamagnetic ferrite particles embedded in starch matrix particles and of a hepatobiliary paramagnetic contrast agent (CrHIDA) results in the production of greatly improved magnetic resonance images of the hepatobiliary system. With the superparamagnetic particles alone, a negative contrast effect was observed in the liver but the biliary system could not be observed. With CrHIDA at doses at which it has a positive contrast effect, the imaging of the gall bladder was enhanced but it was not possible to observe the bile ducts in the liver; however on administration of both the positive and negative MRI contrast agents, the biliary tree, including very tiny bile ducts in the liver, could be observed. Thus the combination of positive and negative tissue specific MRI contrast agents allowed in vivo imaging of the anatomical structure of the liver to an extent that was not possible using either of the agents separately.

The preferred dosages of the positive and negative contrast agents used according to the present invention will vary over a wide range and the chosen dosage will depend upon such factors as the administration route, the nature of the subject, the biodistribution, pharmacokinetics and chemical nature of the contrast agents, and the magnetic field strength and pulse sequence used in the imaging routine. In general, the dosages will be similar to the dosages suggested for the paramagnetic, ferromagnetic and superparamagnetic contrast agents used alone. Conveniently, the dosage for a paramagnetic positive or negative contrast agent will be in the range of 0.001 to 10 mmol/kg bodyweight, especially 0.01-1 mmol/kg bodyweight, while the dosage for a ferromagnetic or, preferably, superparamagnetic substance will be in the range 0.0001 to 5 mmol/kg bodyweight, preferably 0.001-1 mmol Fe/kg bodyweight.

The contrast agent compositions used according to the present invention may of course contain other components besides the paramagnetic, ferromagnetic or superparamagnetic substances and in this regard particular mention may be made of viscosity modifiers, flavourings, pH adjusting agents, osmolality regulators, stabilizers, antioxidants, buffers and emulsifying or dispersing agents as well as other conventional pharmaceutical or veterinary formulation aids.

The contrast media may be formulated in conventional pharmaceutical administration forms, such as tablets, capsules, powders, solutions, suspensions, dispersions, syrups, suppositories, etc.; however, solutions, suspensions and dispersions in physiologically acceptable carrier media, for example water for injections or physiological saline, will generally be preferred.

Where the medium is formulated for parenteral administration, the carrier medium incorporating the magnetic substances will preferably be isotonic or somewhat hypertonic.

For magnetic resonance diagnostic examination, the paramagnetic substance, if in solution, suspension or dispersion form, will generally contain the paramagnetic metal species at a concentration in the range 1 micromole to 1.5 mole per litre, preferably 0.01 to 1000 millimole.

The composition may however be supplied in a more concentrated form for dilution prior to administration. The ferromagnetic or superparamagnetic substance will generally be presented in the form of a suspension or dispersion at a concentration of 0.001 to 10 mol/liter iron. Again, it may be supplied in a more concentrated form for dilution prior to administration.

Where the method of the invention involves parenteral administration of a particle-containing composition, it may be desirable to sonicate the composition before administration to ensure uniform dispersion of the particles; this may however be unnecessary for many superparamagnetic dispersions.

The present invention will now be illustrated further by reference to the following non-limiting Examples in which ratios, percentages and parts referred to are by weight unless otherwise indicated:

EXAMPLE 1

Intravenous contrast agent for visualization of the liver and biliary system

| Composition: | |
| --- | --- |
| Meglumine salt of the chromium (III) chelate of N-(2,6-diethylphenyl-carbamoylmethyl)iminodiacetic acid (i.e. CrHIDA) | 1333 mg |
| Starch-magnetite particles | 200 mg |
| Aqua purificata ad | 20 ml |

The meglumine salt of the chromium (III) chelate of N-(2,6-diethyl-phenylcarbamoylmethyl)-iminodiacetic acid was prepared in accordance with Example 12 of EP-A-165728 and dissolved in distilled water. Starch-magnetite particles (0.1–0.7 micrometer diameter containing 70% by weight iron) were prepared by the Schröder method and added to the red solution of the chromium chelate. The mixture was sonicated for 5 minutes followed by sterilization. The product was filled into a 20 ml vial. Each vial contained 0.075 mmol Cr/ml and 20 mg starch-magnetite particles/ml.

EXAMPLE 2

Parenteral contrast agent for visualization of liver and spleen together with the vascular system in these organs

| Composition: | |
| --- | --- |
| Gadolinium(III)DTPA-beta-alanine-dextran | 78.6 mg |
| Dextran-magnetite-complex | 50 mg |
| Saline solution (0.9% sodium chloride) ad | 10 ml |

Gadolinium(III)DTPA-beta-alanine-dextran, prepared in accordance with Example 3 below, was dissolved in 0.9% sodium chloride solution. Superparamagnetic dextran-magnetite (from Meito Sangyo, Japan) was added. The mixture was sonicated for 5 minutes and sterilized. The product was filled into a 10 ml vial. The vial contained 0.05 mmol Gd/ml and 5 mg dextran-magnetite complex/ml.

EXAMPLE 3

GdDTPA-beta-alanine-dextran (Molecular Weight 70,000)

To a solution of 15.9 g of dextran (molecular weight 70,000, available from Sigma Chemicals) in 650 ml of dry dimethyl sulphoxide (DMSO) was added 20.3 g of fluorenylmethyloxycarbonyl-beta-alanine, 13.7 g of N-ethyl-N'-(3-dimethylaminopropyl)-carbodiimide and 968 mg of 4-pyrrolidino-pyridine dissolved in 350 ml of dry DMSO. The reaction mixture was stirred at ambient temperature for 18 hours and 43.1 g of piperidine was added. After 70 minutes, 7.3 ml of concentrated hydrochloric acid was added dropwise, and cooling on an ice/water bath and dropwise addition of 1.7 l of an ether/chloroform mixture (7:3 w/w) yielded a yellow oil. After decantation, the oil was dissolved in distilled water and the pH was adjusted to 4. Sodium chloride was added until the salt concentration was 0.9% in 1400 ml of solution, and the product was dialyzed against 0.9% sodium chloride in water at pH 4 in a hollow fibre cartridge (Amicon HP 10-20) for 24 hours. The solution was then concentrated using the same equipment against distilled water to a volume of 1150 ml, the pH was adjusted to 9 with N-methylmorpholine and 29.18 g of DTPA-bis-anhydride was added while the pH was kept at 8 using the same base. When the solution became clear, the reaction mixture was stirred for 2 hours, 43.78 g of citric acid dissolved in 47.4 ml of 10 N NaOH was added, and the pH was adjusted to 6.0 with concentrated hydrochloric acid. 30.37 g of gadolinium chloride hexahydrate dissolved in 200 ml of distilled water were added quickly and the pH was adjusted to 5.5 using 10 NaOH. The solution was dialyzed against distilled water until the relaxation time $T_1$ (determined using a NMR Proton Spin Analyzer, RADX Corporation, Houston, Tex., USA, at 10 MHz and 37° C.) was above 2000 ms. Lyophilization of the solution yielded 15.3 g of a light yellow coloured powder.

ANALYSIS

Elemental analysis:

Gd 4.6%; N 2.15%; Na 0.16%; Cl less than 0.01%.

Free Gd (xylene orange titration), DTPA, GdDTPA, citric acid, or DMSO (HPLC): less than 0.01% (The percentages in the analysis results are by weight).

EXAMPLE 4

Kit of two different contrast agents—suspension for oral administration to obtain a negative contrast effect in the gastrointestinal tract and solution for intravenous administration to obtain positive contrast enhancement of the hepatobiliary system

| Suspension for oral administration: | |
| --- | --- |
| Magnetic particles | 1.0 g |
| Hydroxyethyl cellulose | 10.0 g |
| Methyl parahydroxybenzoate | 0.8 g |
| Propyl parahydroxybenzoate | 0.2 g |
| Ethanol | 10.0 g |
| Saccharin sodium | 1.0 g |
| Orange essence | 0.3 g |
| Apricot essence | 0.7 g |
| Water ad | 1000 ml |

Hydroxyethyl cellulose was dispersed in water with stirring for 2 hours. Saccharin sodium and a solution of the essences, methyl and propyl parahydroxybenzoate in ethanol were slowly added. Magnetic particles (3 micrometer in size and containing 19.4% by weight iron) were prepared in accordance with WO 83/01738 (particle type 1) and dispersed in the solution under vigorous stirring. The suspension was filled into a 1000 ml bottle. The suspension contained 194 mg iron.

| -continued | |
|---|---|
| Aqua Purificata ad | 10 ml |

The gadolinium(III) salt is dissolved in distilled water. The solution is filled into a 10 ml vial and heat sterilized.

EXAMPLE 5

Intravenous paramagnetic contrast agent

An injection solution is prepared containing:

| CrHIDA | 6.67 g |
|---|---|
| Water for injections ad | 100 ml |

The chromium salt is dissolved in the water for injections, sterile filtered through 0.22 micrometer millipore filter and filled into 10 ml vials under aseptic conditions.

EXAMPLE 6

Intravenous superparamagnetic contrast agent

An injectable dispersion is prepared which contains:

| Magnetic particles | 30 mg |
|---|---|
| Water for injections ad | 10 ml |

The magnetic particles, which are prepared according to Example 7 below, are dispersed in the water for injections and filled into 10 ml vials under aseptic conditions. A kit is made up containing vials of the paramagnetic agent of Example 5 and vials of the superparamagnetic agent of Example 6. The superparamagnetic agent is sonicated before administration to ensure complete dispersion of the magnetic particles.

EXAMPLE 7

Magnetic particles

Using the Schröder method, ferrite particles of a mean particle size of 10 nm are embedded in starch to produce ferrite/starch particles having a mean particle size of 0.7 micrometer (the majority of the particles being in the size range 0.3 to 1.1 micrometers) and an Fe content of about 60% by weight.

EXAMPLE 8

Imaging of the Hepatobiliary system in dogs

Beagle dogs weighing 10 to 12 kg were examined by magnetic resonance imaging under iv pentothal anaesthesia. In eight dogs, examinations were performed over four days before and after i.v. injection of 4 to 8 mgFe/kg bodyweight of superparamagnetic iron oxide (the composition of Example 6). Examinations were made directly, every hour for four hours, every two to three hours up to twelve hours and around 24, 48 and 72 hours after injection of the contrast agent. In three other dogs, examinations were performed before and after i.v. injection of 0.1 to 0.2 mmol/kg bodyweight of CrHIDA (the composition of Example 5). Four further dogs were examined before and after i.v. injection of 2 to 4 mgFe/kg bodyweight of superparamagnetic iron oxide followed after about 30 minutes by 0.2 to 0.4 mmol/kg bodyweight of CrHIDA i.v. Examinations after CrHIDA were made every 10 minutes for 60 minutes.

Examination was by magnetic resonance imaging using a superconductive system (Siemens Magnetom) operating at 0.5 tesla. After CrHIDA administration, examinations were made in the head coil and in the transverse and frontal projections with .7 or 20 mm slice thicknesses in a multislice mode with TR of 0.25 sec and TE of 22 and 35 msec. A gradient echo sequence (FLASH) with an 80° flip angle, TR of 140 ms and TE of 14 ms was used in one examination. In the case of the administration of the superparamagnetic contrast agent alone, multislice transverse images were taken with TR 500, TE 22 and TR 1500, TE 35/70 msec. For $T_1$ measurements, 6 TR of 100, 300, 500, 700, 1500 and 3000 ms with TE 20 ms and for $T_2$ measurements four TE of 30, 60, 94 and 134 ms with TR 1500 ms were used.

In three of the dogs to which the positive and negative contrast agents were administered, 1.0 unit/kg bodyweight of cholecystokinin were given intravenously 60 minutes after administration of the paramagnetic contrast agent immediately followed by examinations in the transverse and frontal projections.

Blood, urine and liver function tests were performed two days after the investigations.

Before contrast administration, the bile ducts were not discernible, while the gall bladder in some cases could be identified because of its slightly higher signal intensity than that of the liver. In the dogs examined after administration of only CrHIDA, the bile ducts were not visible either, although a higher signal intensity was present in the gall bladder after 15 to 30 minutes. The signal intensity of the liver parenchyma or of the muscle did not change significantly after injection of CrHIDA.

After injection of the superparamagnetic contrast agent at a dosage of 2.0 mgFe/kg bodyweight, a pronounced lowering of the signal intensity of the liver was achieved and further reduction of the signal close to the background noise level was present after 4.0 mgFe/kg was noted. The maximum effect was noted after about 30 minutes and thereafter persisted unchanged throughout the measurement. There was no change of the signal intensity of the muscle.

The wider bile ducts were discernible after administration of the superparamagnetic contrast agent as a result of the lowering of the signal intensity from the liver. The gall bladder was also readily discernible. However, after administration of the superparamagnetic contrast agent followed by administration of the paramagnetic contrast agent, the bile ducts exhibited a higher signal intensity and even very tiny bile ducts were visible in the transverse and frontal images. An increased signal intensity from the gall bladder was also encountered 15 to 30 minutes after contrast agent administration. After administration of the superparamagnetic and paramagnetic contrast agents and after cholecystokinin injection, the gall bladder was moderately contracted and visualization of the choledocus duct was achieved as well as contrast filling of the duodenum.

The blood, urine and liver function texts were found to be normal during the experiments.

FIGS. 1 to 3 of the accompanying drawings illustrate the observed enhancement in liver image contrast.

Figure 1C:
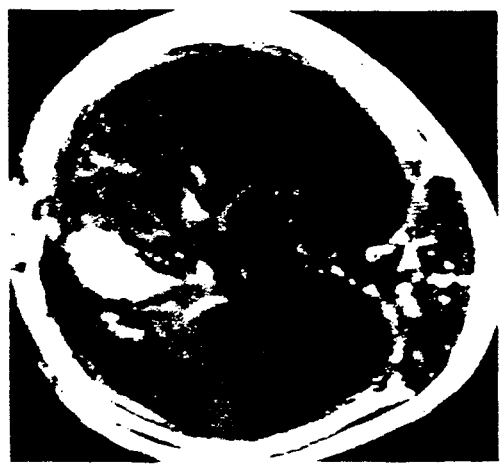
FIGS. 1a, 1b and 1c are transverse images of the liver before contrast agent administration (FIG. 1a), after administration of the negative contrast agent (FIG. 1b) and after administration of both negative and positive contrast agents (FIG. 1c). Small bile ducts not discernible in FIGS. 1a and 1b become visible in FIG. 1c.
Figure 1B:
Figure 1A:
Figure 2C:
FIGS. 2a, 2b and 2c are similarly transverse images of the liver before and after contrast agent administration
Figure 2B:
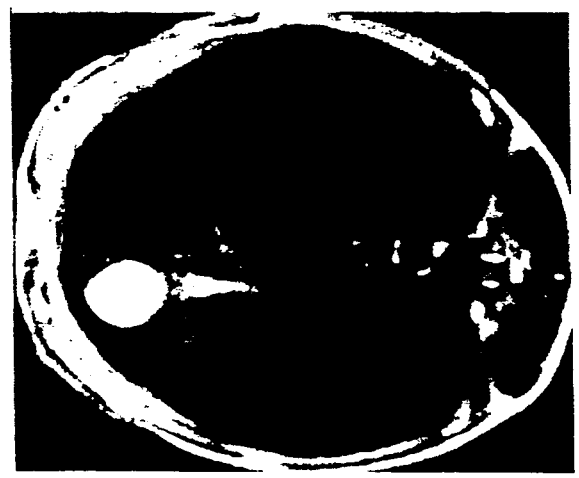
Figure 2A:
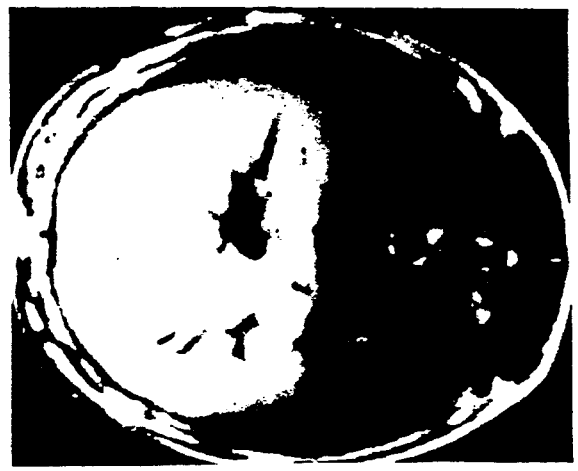
Figure 3C:
FIGS. 3a, 3b and 3c are frontal images of the liver before and after contrast agent administration.
Figure 3B:
Figure 3A:

For FIGS. 1 to 3 the contrast agent dosages are respectively

|  | Negative Agent | Positive Agent |
| --- | --- | --- |
| FIG. 1 (a, b & c) | 2.0 mg Fe/kg | 0.2 mmol/kg Cr HIDA |
| FIG. 2 (a, b & c) | 4.0 mg Fe/kg | 0.4 mmol/kg Cr HIDA |
| FIG. 3 (a, b & c) | 4.0 mg Fe/kg | 0.4 mmol/kg Cr HIDA |

We claim:

1. A magnetic resonance imaging contrast medium comprising at least one physiologically acceptable body tissue- or body duct-specific negative MRI contrast agent together with at least one physiologically acceptable body tissue- or body duct-specific positive MRI contrast agent.

2. A medium as claimed in claim 1 adapted for administration into the cardiovascular system and wherein one or both of said positive and negative agents is a blood-pool agent.

3. A medium as claimed in claim 1 comprising at least one physiologically acceptable paramagnetic substance together with at least one physiologically acceptable ferromagnetic or superparamagnetic substance.

4. A medium as claimed in claim 1 wherein said positive agent comprises a chelate of $Gd^{3+}$, $Cr^{3+}$, $Fe^{3+}$ or $Mn^{2+}$.

5. A medium as claimed in claim 1 wherein said negative agent comprises a chelate of $Dy^{3+}$, $Tb^{3+}$ or $Sm^{3+}$.

6. A medium as claimed in claim 1 where said negative agent comprises superparamagnetic particles carried by particles of physiologically acceptable matrix material.

7. A medium as claimed in claim 1 adapted for administration into the cardiovascular system and comprising superparamagnetic particles carried by particles by a physiologically acceptable matrix material together with a positive contrast agent selected from CrHIDA, FeEHPG and macromolecule-bound chelated paramagnetic metal species having a molecular a weight of at least 40,000.

8. A MRI contrast medium kit comprising a first container containing a negative MRI contrast medium in an administration form adapted for body tissue- or body duct-specific contrast enhancement and a second container separately containing a positive MRI contrast medium in an administration form adapted for body tissue- or body duct-specific contrast enhancement.

9. A kit as claimed in claim 8 wherein said positive and negative media are in forms adapted for administration into different body tissues, ducts or cavities.

10. A method of generating images of the human or non-human animal body, which method comprises administering to said body a diagnostically effective amount of a body tissue- or body duct-specific MRI contrast agent and of a body tissue- or body duct-specific positive MRI contrast agent and generating a magnetic resonance image of a part of said body containing said negative and positive agents or paramagnetic, ferromagnetic, or superparamagnetic biodegradation products thereof.

11. A method as claimed in claim 10 wherein one or both of said positive and negative agents is a blood-pool agent and is administered into the cardiovascular system of said body.

12. A method as claimed in claim 10 wherein said positive and negative agents are administered together.

13. A method as claimed in claim 10 wherein said positive and negative agents are administered via different routes whereby to approach or merge at a selected body site and wherein said image is generated of said selected body site.

14. A method as claimed in claim 10 wherein as said negative agent is administered a particulate ferromagnetic or superparamagnetic material.

15. A method as claimed in claim 10 wherein said negative agent is administered a physiologically acceptable chelate of $Dy^{3+}$, $Tb^{3+}$ or $Sm^{3+}$.

16. A method as claimed in claim 10 wherein as said positive contrast agent is administered a physiologically acceptable chelate of $Gd^{3+}$, $Cr^{3+}$, $Fe^{3+}$ or $Mn^{2+}$.

17. A method as claimed in claim 10 wherein a physiologically acceptable paramagnetic substance is administered as said MRI contrast agent.

* * * * *